United States Patent [19]

Leto et al.

[11] 4,060,932

[45] Dec. 6, 1977

[54] DOLL WITH INTERNAL WARMING MECHANISM

[76] Inventors: Armetia E. Leto, 830 Deer Park Road, Dix Hills, N.Y. 11746; Lawrence H. Bauer, 171 W. 9th St., Deer Park, N.Y. 11729

[21] Appl. No.: 668,958

[22] Filed: Mar. 22, 1976

[51] Int. Cl.² .............................................. A63H 3/24
[52] U.S. Cl. ......................................... 46/116; 46/141
[58] Field of Search .................. 46/116, 141; 132/36.2

[56] References Cited

U.S. PATENT DOCUMENTS

| | | | |
|---|---|---|---|
| 2,239,410 | 4/1941 | Bonat | 132/36.2 B |
| 2,774,184 | 12/1956 | Hefferan et al. | 46/116 |
| 3,016,651 | 1/1962 | Brudney | 46/141 |
| 3,535,246 | 10/1970 | Crowell | 252/70 |

*Primary Examiner*—Russell R. Kinsey
*Assistant Examiner*—Robert F. Cutting
*Attorney, Agent, or Firm*—Bauer, Amer & King

[57] ABSTRACT

A doll simulating a warm-blooded human baby or other mammal form is provided with an internal vessel containing an exothermic salt and means to introduce water into the vessel to activate the salt to release heat. The heat is transferred to the wall of the doll to provide a feeling of body warmth.

11 Claims, 7 Drawing Figures

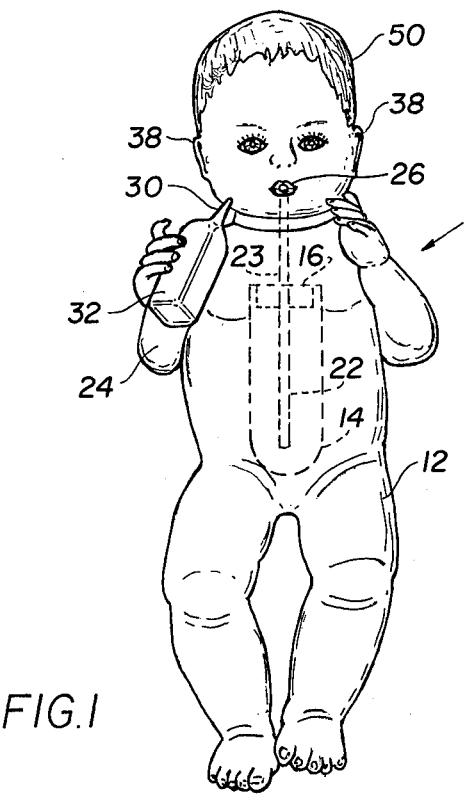
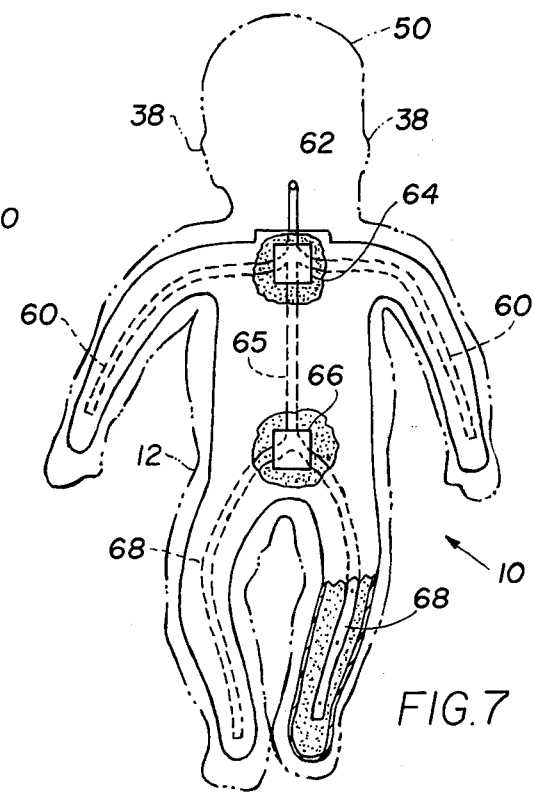
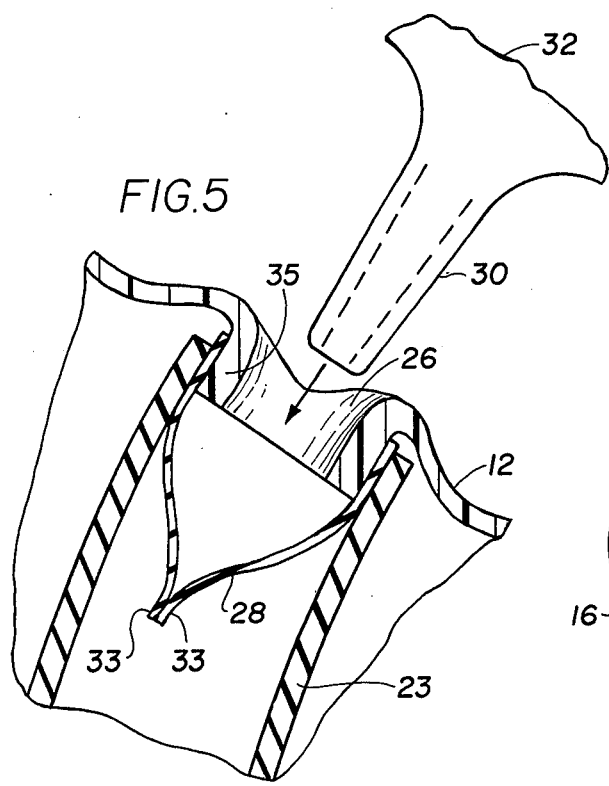
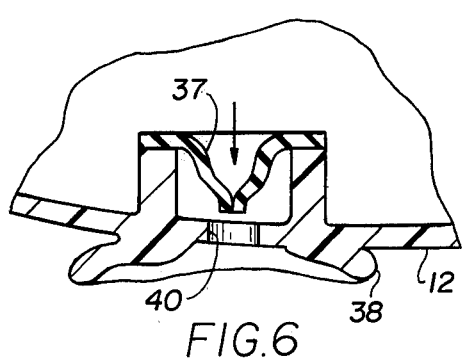
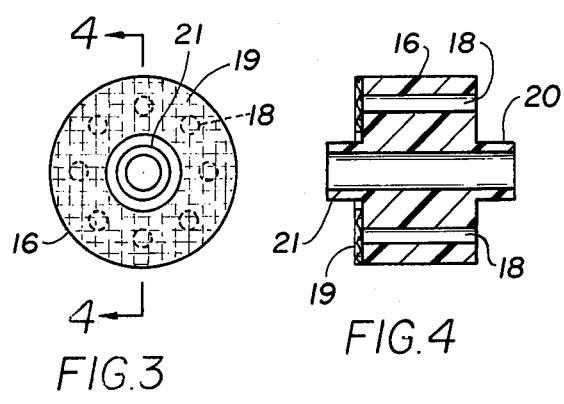

4,060,932

DOLL WITH INTERNAL WARMING MECHANISM

BRIEF SUMMARY OF THE INVENTION

A doll body simulates a warm-blooded mammal, which may be a human or animal form. The skin of the doll is made of a heat conductive plastic, such as polyvinyl. Within the body there is positioned a pouch containing an exothermic salt. A conduit leads from a mouth member to the pouch and receives sufficient water from a bottle to activate the quantity of exothermic salt in the pouch to heat the doll. A one-way valve provides a pumping action, drawing the water into the pouch when the doll is squeezed. A second conduit connects the pouch to the atmosphere to permit the escape of gases. The bottle is fitted with a nipple, which fits a mouth opening leading to the conduit in an airtight relationship.

The present invention relates to dolls and, in particular, to such articles having internal warming means.

BACKGROUND OF THE INVENTION

Dolls are generally cold to the touch and it is desirable to impart a feeling of warmth such as that exuded by a human body, a puppy, or other mammal when handled by a child. For reasons of practicality, such a doll should be heated by independent means. Thus, the use of electrical heating, where the doll is connected by an electric cord to an outlet, is considered undesirable, firstly, because of the potential danger of a toy connected to a high voltage electrical outlet and, secondly, it limits the movements of the child while playing with the doll.

Accordingly, it is an object of this invention to provide a doll with self-contained, internal warming means.

it is a further object of this invention to provide a doll having a container of exothermic salts and means for introducing sufficient water into said container to cause said exothermic salts to generate heat.

The above description, as well as further objects, features and advantages of the present invention, will be more fully appreciated by reference to the following detailed description of a presently preferred, but nonetheless illustrative, embodiment in accordance with the present invention when taken in conjunction with the accompanying drawings wherein:

FIG. 1 is a front elevational view of a doll embodying a heating mechanism which is shown in phantom;

FIG. 3 is a top plan view of a connector employed in the doll;

FIG. 4 is a sectional view taken along line 4—4 of FIG. 3;

FIG. 5 is a sectional view of the lips of the doll, a valve and a portion of a nipple affixed to a supply bottle;

FIG. 6 is a sectional view of the doll's ear and a valve therein; and

FIG. 7 is a plan view, partially broken away, of a heating means for heating the extremities of a doll shown in phantom.

DESCRIPTION OF THE PREFERRED EMBODIMENT

Figure 2:
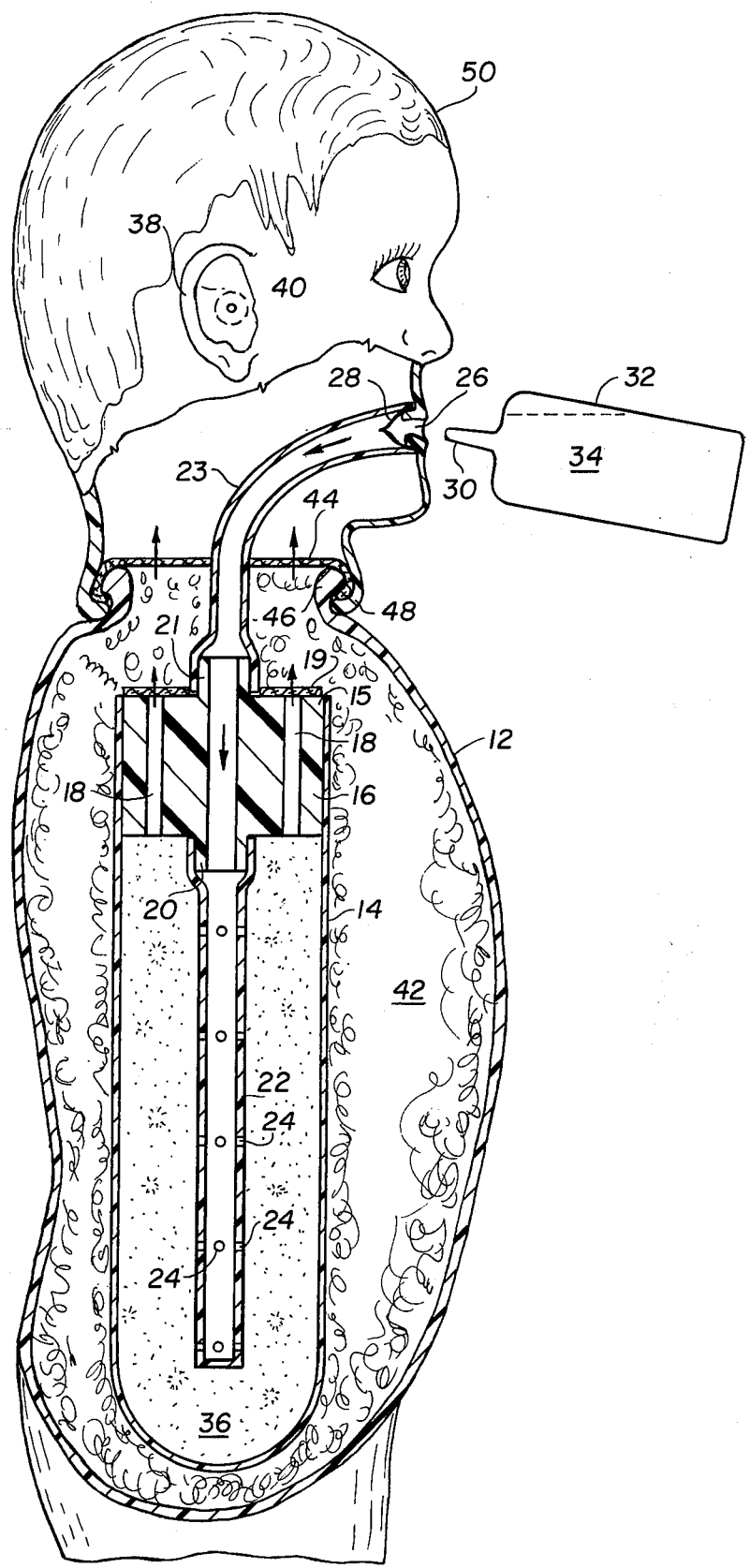
FIG. 2 is a side elevational sectional view of a portion of the doll of FIG. 1 and part of it broken away.

Reference is now made to FIG. 1 of the drawing, where there is shown a doll 10 simulating a human baby. It is to be understood, however, as the following description proceeds, that the invention applies to the simulation of any warm-blooded mammal and is not to be construed as limited to a human form.

As shown in FIG. 2, the outer shell 12 of the doll is composed of a non-porous soft plastic such as a vinyl plastic, which may be formed from a plastisol in a hollow mold by conventional techniques to prevent the passage of liquid through the wall thereof. A fluid-tight vessel 14, preferably plastic, is positioned within the body 12 and has its end orifice 15 closed by a plug 16. As shown in FIGS. 3 and 4, plug 16 is provided with a number of bores 18 extending through the plug body. Tubular nipples 20 and 21 extending from the plug body 16 receive tubes 22 and 23.

Tube 23 leads from nipple 21 to a mouth portion 26. A valve 28, described more fully hereinafter, opens into tube 23 when the nipple 30 of a bottle 32 is inserted in the mouth orifice 26. The bottle 32 is of such size as to limit its capacity to a sufficient quantity of water 34 to activate the exothermic salt 36 disposed within vessel 14. It will be noted that tube 22 is provided with a plurality of openings 24 disposed along and about the tube 22 to distribute the water into the vessel 14 so as to uniformly activate the exothermic salt 36 therein.

By way of example, a suitable flutter type valve 28 is shown in FIG. 5. One end of the valve 28 is normally closed by mating lips 33 that open under pressure and by the insertion of the bottle nipple 33 while the other end of the valve 28 terminates in a sleeve portion 35 which is captured between the inwardly extending tubular mouth portion 26 and the tube 23. The members may be force fit to secure them together and can be additionally, or alternatively, solvent or heat-sealed thereto.

As the body 12 is cuddled by a child, it is squeezed and compressed, forcing air through a one-way valve 37 oriented to vent the air into the atmosphere. The valve 37 may be conveniently hidden within the doll's ear 38 and vented at an orifice 40. In turn, releasing the pressure on the body 12 permits it to expand and create a vacuum, which draws the water through one-way valve 28 from the bottle 32 to activate the exothermic salt.

The water flows by gravity through tube 23 into tube 22 and dispersed therefrom at openings 24 into the exothermic salt 36. Heat released by the chemical action of the salt is transmitted through the walls of vessel 14 and through a heat conductive, or at least relatively poor heat insulating filling 42 to the outer wall 12. The filling 42 may consist of a cotton wadding, synthetic fibers, pieces of foam rubber or plastic, such as polyurethane foam. As the exothermic salt 36 heats up, water will be evaporated and will pass through orifices 18 of plug 16. To assure that the salt is retained within the vessel 14, the orifices 18 may be covered by a fine mesh screen 19 to prevent the fine salt particles from escaping from the vessel 14 and effectively close the same.

Elasticized nylon cover 44 fits tight around the neck 46 of the body 12 and held in such position by a locking connector 48 of the head 50. The cover 44 permits air and water vapors to pass therethrough to the ear vent 40 and out to the atmosphere. A child cuddling the doll 10 will feel its warmth and, if the skin is of the vinyl type, the doll will feel human and alive. The exothermic salt employed should be of a type which is non-toxic and preferably can be reactivated for reuse by drying out the salt as the air and water vapors exhaust through the vent 40. Exothermic salts are disclosed, for example, in U.S. Pat. No. 3,535,246.

Vessel 14 may be made of heat-sealed flexible plastic film, such as vinyl or polyethylene having a thickness of about 10 mils or of a rigid or semi-rigid plastic container, produced by injection molding or blow molding. The container 14 for the exothermic material 36 may be extended in length to conform to the shape of the torso and limbs of the doll 10 as shown in FIG. 7. For this purpose, the aforementioned flexible container construction may be made to include a tube 62 that leads from the mouth orifice to a junction block 64. Water is distributed from junction 64 to perforated tubes 60 in the arm portions and to tube 65, which leads to a junction block 66, which distributes water to perforated leg tubes 68. In this manner, the whole or substantially the whole of the doll 10 may exude the heat of the exothermic salt and its chemical reaction.

The head 50 may be hollow, as shown in the drawing, or may be filled. In the latter case, a conduit is provided from the container 14 to the orifice 40 communicating with the atmosphere in the manner as described previously. In this case, the configuration of plug 16 may be changed to have two equal diameter passages in lieu of 8 small holes and one large hole as shown in FIGS. 3 and 4. One passage may still connect tube 23 and tube 22 while the other will connect volume 36 with 37 and 40 as shown in FIG. 6. The additional conduit may be fitted with a fine mesh filter similar to 19.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. A doll simulating a warm-blooded mammal comprising
   a head, torso and limb portions,
   a non-porous heat conductive skin covering said portions,
   a quantity of an exothermic salt contained within at least one of said portions, said quantity of said salt being sufficient, when wet, to produce heat to warm said skin to a temperature simulating that of a warm-blooded mammal,
   and fluid communication means extending from the outside of said skin to said salt for wetting and drying said salt.

2. The doll of claim 1 wherein said doll simulates a human baby.

3. The doll of claim 1 including an effectively closed vessel in said one portion containing said exothermic salt.

4. The doll of claim 3 including an orifice extending through said skin and connected with said fluid communication means for forming a fluid communication between said vessel and said orifice.

5. The doll of claim 4 including a one-way valve interposed between said orifice and said vessel and oriented for restricting fluid flow in one direction between said vessel and orifice.

6. The doll of claim 5 wherein said fluid communication means includes a conduit member extending into said vessel from said orifice to enable the flow of fluid from said orifice into said vessel.

7. The doll of claim 4 wherein said fluid communication means includes at least an escape opening in said vessel communicating with an orifice in said skin to enable the escape of fluid from said vessel.

8. The doll of claim 7 wherein said vessel extends into said limb portions.

9. An apparatus for simulating a warm-blooded mammal comprising
   a body portion in the configuration of a mammal, including torso, limb and head portions,
   a non-porous plastic heat conductive skin enclosing said apparatus,
   a fluid-tight container in said body portion having a fluid input orifice,
   conduit means extending from an inlet opening in said skin extending from outside of said body to said input orifice,
   a quantity of exothermic salt within said container sufficient to warm said skin when activated by water supplied thereto from said opening,
   heat transfer filler material occupying the space between said skin and said container,
   and a fluid outlet opening in said skin communicating with said container and said exothermic salt to permit the exhaust of fluid therefrom.

10. In combination with the apparatus of claim 9,
    a bottle having a nipple adapted to fit said inlet opening in an air-tight relationship,
    said bottle having a volume sufficient to supply a quantity of water to said salt to activate said exothermic salt to heat said body.

11. A heatable doll comprising
    a non-porous skin,
    a container in said doll,
    a quantity of exothermic salt in said container for activation by a fluid to exude heat that is felt at the skin,
    opening means on said skin,
    and fluid communication means between said opening means to communicate activating fluid to said salt from outside said skin and to permit the evaporation of said activating fluid from said salt to enable said salt to dry for reuse.

* * * * *